US012678147B2

(12) United States Patent
Romo

(10) Patent No.: US 12,678,147 B2
(45) Date of Patent: Jul. 14, 2026

(54) METHOD, APPARATUS, AND SYSTEM FOR FACILITATING BENDING OF AN INSTRUMENT IN A SURGICAL OR MEDICAL ROBOTIC ENVIRONMENT

(71) Applicant: Auris Health, Inc., Redwood City, CA (US)

(72) Inventor: Enrique Romo, Dublin, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 18/215,762

(22) Filed: Jun. 28, 2023

(65) Prior Publication Data

US 2023/0414210 A1 Dec. 28, 2023

Related U.S. Application Data

(63) Continuation of application No. 16/115,389, filed on Aug. 28, 2018, now Pat. No. 11,723,636, which is a
(Continued)

(51) Int. Cl.
*A61B 17/00* (2006.01)
*A61B 1/005* (2006.01)
(Continued)

(52) U.S. Cl.
CPC ...... *A61B 17/00234* (2013.01); *A61B 1/0055* (2013.01); *A61B 1/0056* (2013.01);
(Continued)

(58) Field of Classification Search
CPC ............ A61B 17/00234; A61B 1/0055; A61B 1/0056; A61B 34/30; A61B 2034/301;
(Continued)

(56) References Cited

U.S. PATENT DOCUMENTS 3,572,325 A 3/1971 Bazell et al.
3,913,565 A 10/1975 Kawahara
(Continued)

FOREIGN PATENT DOCUMENTS

CH 690088 4/2000
CN 1839764 A 10/2006
(Continued)

OTHER PUBLICATIONS

Advisory Action for U.S. Appl. No. 14/201,610, dated Jun. 19, 2017, 2 pages.
(Continued)

*Primary Examiner* — Anh T Nguyen
*Assistant Examiner* — Shankar Raj Ghimire
(74) *Attorney, Agent, or Firm* — Vorys, Sater, Seymour and Pease LLP

(57) ABSTRACT

A method, apparatus, and system for facilitating bending of an instrument in a surgical or medical robotic environment are provided. In one aspect, a surgical system includes an instrument comprising an end effector, the instrument capable of articulation via a bending section. The bending section includes a body including a first strut and a second strut, and a channel formed through the body. The first strut and the second strut form a gap therebetween, wherein the gap is in communication with the channel formed through the body.

19 Claims, 8 Drawing Sheets

Related U.S. Application Data continuation of application No. 14/201,610, filed on Mar. 7, 2014, now Pat. No. 10,149,720.

(60) Provisional application No. 61/774,901, filed on Mar. 8, 2013.

(51) Int. Cl.
　　*A61B 34/30*　　　(2016.01)
　　*A61M 25/01*　　　(2006.01)

(52) U.S. Cl.
　　CPC ......... *A61B 34/30* (2016.02); *A61M 25/0138* (2013.01); *A61M 25/0147* (2013.01); *A61B 2034/301* (2016.02); *A61B 2034/306* (2016.02); *Y10T 74/20323* (2015.01)

(58) Field of Classification Search
　　CPC ......... A61B 2034/306; A61M 25/0138; Y10T 74/20323
　　See application file for complete search history.

(56) References Cited

U.S. PATENT DOCUMENTS

| | | | |
|---|---|---|---|
| 4,294,234 A | | 10/1981 | Matsuo |
| 4,392,485 A | | 7/1983 | Hiltebrandt |
| 4,580,551 A | * | 4/1986 | Siegmund ............ A61B 1/0055 |
| | | | 600/139 |
| 4,597,388 A | | 7/1986 | Koziol et al. |
| 4,607,619 A | | 8/1986 | Seike et al. |
| 4,690,175 A | | 9/1987 | Ouchi et al. |
| 4,700,693 A | | 10/1987 | Lia et al. |
| 4,706,656 A | | 11/1987 | Kuboto |
| 4,721,097 A | | 1/1988 | D'Amelio |
| 4,741,326 A | | 5/1988 | Sidall et al. |
| 4,745,908 A | | 5/1988 | Wardle |
| 4,748,969 A | | 6/1988 | Wardle |
| 4,750,475 A | | 6/1988 | Yoshihashi |
| 4,771,766 A | | 9/1988 | Aoshiro et al. |
| 4,846,791 A | | 7/1989 | Hattler et al. |
| 4,869,238 A | | 9/1989 | Opie et al. |
| 4,905,673 A | | 3/1990 | Pimiskern |
| 4,906,496 A | | 3/1990 | Hosono et al. |
| 4,907,168 A | | 3/1990 | Boggs |
| 4,911,148 A | | 3/1990 | Sosnowski et al. |
| 4,967,732 A | | 11/1990 | Inoue |
| 5,050,585 A | | 9/1991 | Takahashi |
| 5,083,549 A | | 1/1992 | Cho et al. |
| 5,106,387 A | | 4/1992 | Kittrell et al. |
| 5,108,800 A | | 4/1992 | Koo |
| 5,125,909 A | | 6/1992 | Heimberger |
| 5,168,864 A | | 12/1992 | Shockey |
| 5,217,002 A | | 6/1993 | Katsurada et al. |
| 5,251,611 A | | 10/1993 | Zehel et al. |
| 5,257,617 A | | 11/1993 | Takahashi |
| 5,261,391 A | | 11/1993 | Inoue |
| 5,271,381 A | * | 12/1993 | Ailinger ............... A61B 1/0055 |
| | | | 600/128 |
| 5,287,861 A | | 2/1994 | Wilk |
| 5,313,934 A | | 5/1994 | Wiita et al. |
| 5,381,782 A | | 1/1995 | DeLaRama et al. |
| 5,386,818 A | | 2/1995 | Schneebaum et al. |
| 5,425,735 A | | 6/1995 | Rosen et al. |
| 5,448,988 A | | 9/1995 | Watanabe |
| 5,462,561 A | | 10/1995 | Voda |
| 5,472,406 A | | 12/1995 | Torre et al. |
| 5,477,856 A | * | 12/1995 | Lundquist ......... A61M 25/0136 |
| | | | 607/122 |
| 5,478,330 A | | 12/1995 | Imran et al. |
| 5,482,029 A | | 1/1996 | Sekiguchi et al. |
| 5,489,270 A | | 2/1996 | Erp |
| 5,507,725 A | | 4/1996 | Savage et al. |
| 5,507,751 A | * | 4/1996 | Goode ............ A61B 17/32075 |
| | | | 606/108 |

| | | | |
|---|---|---|---|
| 5,533,985 A | | 7/1996 | Wang |
| 5,572,999 A | | 11/1996 | Funda et al. |
| 5,580,200 A | | 12/1996 | Fullerton |
| 5,662,590 A | | 9/1997 | Torre et al. |
| 5,681,296 A | | 10/1997 | Ishida |
| 5,695,500 A | | 12/1997 | Taylor et al. |
| 5,704,534 A | | 1/1998 | Huitema et al. |
| 5,720,775 A | | 2/1998 | Lamard |
| 5,741,429 A | | 4/1998 | Donadio, III et al. |
| 5,749,889 A | | 5/1998 | Bacich et al. |
| 5,833,632 A | * | 11/1998 | Jacobsen .............. A61M 25/09 |
| | | | 606/41 |
| 5,873,817 A | | 2/1999 | Kokish et al. |
| 5,876,325 A | | 3/1999 | Mizuno et al. |
| 5,879,287 A | | 3/1999 | Yoshihashi |
| 5,882,347 A | | 3/1999 | Mouris-Laan et al. |
| 5,888,191 A | | 3/1999 | Akiba et al. |
| 5,910,129 A | | 6/1999 | Koblish et al. |
| 5,928,163 A | | 7/1999 | Roberts et al. |
| 5,938,586 A | | 8/1999 | Wilk et al. |
| 5,938,587 A | | 8/1999 | Taylor et al. |
| 6,012,494 A | | 1/2000 | Balazs |
| 6,019,772 A | | 2/2000 | Shefaram et al. |
| 6,033,371 A | | 3/2000 | Torre et al. |
| 6,143,013 A | | 11/2000 | Samson et al. |
| 6,157,853 A | | 12/2000 | Blume et al. |
| 6,174,280 B1 | | 1/2001 | Oneda et al. |
| 6,197,015 B1 | | 3/2001 | Wilson |
| 6,198,974 B1 | | 3/2001 | Webster, Jr. |
| 6,234,958 B1 | | 5/2001 | Snoke et al. |
| 6,315,715 B1 | * | 11/2001 | Taylor ................... A61B 1/018 |
| | | | 138/122 |
| 6,326,616 B1 | | 12/2001 | Andrien, Jr. et al. |
| 6,398,792 B1 | | 6/2002 | O'Connor |
| 6,404,497 B1 | | 6/2002 | Backman et al. |
| 6,406,486 B1 | | 6/2002 | Torre et al. |
| 6,428,489 B1 | * | 8/2002 | Jacobsen .............. A61M 25/09 |
| | | | 600/585 |
| 6,436,107 B1 | | 8/2002 | Wang et al. |
| 6,464,632 B1 | | 10/2002 | Taylor |
| 6,485,411 B1 | | 11/2002 | Konstorum et al. |
| 6,491,626 B1 | * | 12/2002 | Stone ........................ F16D 1/00 |
| | | | 403/291 |
| 6,537,205 B1 | | 3/2003 | Smith |
| 6,554,793 B1 | | 4/2003 | Pauker et al. |
| 6,579,246 B2 | * | 6/2003 | Jacobsen .............. A61M 25/09 |
| | | | 600/585 |
| 6,638,246 B1 | | 10/2003 | Naimark et al. |
| 6,671,581 B2 | | 12/2003 | Niemeyer et al. |
| 6,716,178 B1 | | 4/2004 | Kilpatrick et al. |
| 6,736,784 B1 | | 5/2004 | Menne et al. |
| 6,746,422 B1 | | 6/2004 | Noriega et al. |
| 6,749,560 B1 | * | 6/2004 | Konstorum ........ A61B 1/00071 |
| | | | 604/525 |
| 6,763,259 B1 | | 7/2004 | Hauger et al. |
| 6,790,173 B2 | | 9/2004 | Saadat et al. |
| 6,827,710 B1 | | 12/2004 | Mooney et al. |
| 6,827,712 B2 | | 12/2004 | Tovey et al. |
| 6,837,846 B2 | | 1/2005 | Jaffe et al. |
| 6,908,428 B2 | | 6/2005 | Aizenfeld et al. |
| 6,921,362 B2 | | 7/2005 | Ouchi |
| 6,932,824 B1 | | 8/2005 | Roop et al. |
| 6,958,035 B2 | | 10/2005 | Friedman et al. |
| 7,008,401 B2 | | 3/2006 | Thompson et al. |
| 7,087,061 B2 | | 8/2006 | Chernenko et al. |
| 7,130,700 B2 | | 10/2006 | Gardeski et al. |
| 7,217,246 B1 | * | 5/2007 | Stone ............... A61B 17/00234 |
| | | | 600/585 |
| 7,344,528 B1 | | 3/2008 | Tu et al. |
| 7,351,193 B2 | | 4/2008 | Forman et al. |
| 7,594,903 B2 | | 9/2009 | Webler et al. |
| 7,615,067 B2 | * | 11/2009 | Lee ....................... A61B 1/0057 |
| | | | 606/205 |
| 7,645,230 B2 | | 1/2010 | Mikkaichi et al. |
| 7,645,231 B2 | | 1/2010 | Akiba |
| 7,678,117 B2 | * | 3/2010 | Hinman ................. A61B 17/29 |
| | | | 606/1 |
| 7,725,214 B2 | | 5/2010 | Diolaiti |

(56)            References Cited

U.S. PATENT DOCUMENTS

| | | | |
|---|---|---|---|
| 7,789,827 B2 | 9/2010 | Landry | |
| 7,828,724 B2 * | 11/2010 | Hosoi | A61B 1/005 |
| | | | 600/142 |
| 7,842,028 B2 * | 11/2010 | Lee | A61B 17/3403 |
| | | | 606/1 |
| 7,883,475 B2 | 2/2011 | Dupont et al. | |
| 7,918,845 B2 * | 4/2011 | Saadat | A61B 1/018 |
| | | | 606/1 |
| 7,930,065 B2 | 4/2011 | Larkin et al. | |
| 7,967,799 B2 | 6/2011 | Boukhny | |
| 8,046,049 B2 | 10/2011 | Govari et al. | |
| 8,049,873 B2 | 11/2011 | Hauger et al. | |
| 8,052,597 B2 * | 11/2011 | Boulais | A61B 1/0057 |
| | | | 600/141 |
| 8,052,636 B2 | 11/2011 | Moll et al. | |
| 8,224,484 B2 | 7/2012 | Swarup et al. | |
| 8,246,536 B2 | 8/2012 | Ochi et al. | |
| 8,256,428 B2 * | 9/2012 | Hindricks | A61B 18/1492 |
| | | | 606/1 |
| 8,292,827 B2 | 10/2012 | Musbach et al. | |
| 8,347,754 B1 * | 1/2013 | Veltri | A61B 34/30 |
| | | | 606/1 |
| 8,409,245 B2 * | 4/2013 | Lee | A61B 17/29 |
| | | | 606/205 |
| 8,414,564 B2 | 4/2013 | Goldshleger et al. | |
| 8,444,637 B2 | 5/2013 | Podmore et al. | |
| 8,460,236 B2 | 6/2013 | Roelle et al. | |
| 8,498,691 B2 | 7/2013 | Moll et al. | |
| 8,515,215 B2 | 8/2013 | Younge et al. | |
| 8,518,024 B2 | 8/2013 | Williams et al. | |
| 8,602,031 B2 | 12/2013 | Reis et al. | |
| 8,652,030 B2 | 2/2014 | Matsuura et al. | |
| 8,684,953 B2 * | 4/2014 | Cabiri | A61M 25/0147 |
| | | | 600/585 |
| 8,686,747 B2 | 4/2014 | Berner et al. | |
| 8,720,448 B2 | 5/2014 | Reis et al. | |
| 8,758,231 B2 | 6/2014 | Bunch et al. | |
| 8,764,743 B2 * | 7/2014 | McDaniel | A61B 18/1492 |
| | | | 138/119 |
| 8,821,477 B2 | 9/2014 | Northrop et al. | |
| 8,827,947 B2 | 9/2014 | Bosman et al. | |
| 8,827,948 B2 | 9/2014 | Romo et al. | |
| 8,894,610 B2 | 11/2014 | Macnamara et al. | |
| 8,961,533 B2 | 2/2015 | Stahler et al. | |
| 9,186,046 B2 | 11/2015 | Ramamurthy et al. | |
| 9,204,933 B2 | 12/2015 | Reis et al. | |
| 9,220,398 B2 * | 12/2015 | Woodley | B25J 18/06 |
| 9,254,123 B2 | 2/2016 | Alvarez et al. | |
| 9,314,953 B2 | 4/2016 | Lauer et al. | |
| 9,408,669 B2 | 8/2016 | Kokish et al. | |
| 9,427,551 B2 | 8/2016 | Eeflang et al. | |
| 9,462,932 B2 | 10/2016 | Ostrovsky et al. | |
| 9,504,604 B2 | 11/2016 | Alvarez | |
| 9,561,083 B2 | 2/2017 | Yu et al. | |
| 9,591,990 B2 | 3/2017 | Chen et al. | |
| 9,622,827 B2 | 4/2017 | Yu et al. | |
| 9,636,184 B2 | 5/2017 | Lee et al. | |
| 9,713,509 B2 | 7/2017 | Schuh et al. | |
| 9,727,963 B2 | 8/2017 | Mintz et al. | |
| 9,730,572 B2 | 8/2017 | Hasser et al. | |
| 9,737,371 B2 | 8/2017 | Romo et al. | |
| 9,737,373 B2 | 8/2017 | Schuh | |
| 9,744,335 B2 | 8/2017 | Jiang | |
| 9,763,741 B2 | 9/2017 | Alvarez et al. | |
| 9,788,910 B2 | 10/2017 | Schuh | |
| 9,818,681 B2 | 11/2017 | Machida | |
| 9,844,353 B2 | 12/2017 | Walker et al. | |
| 9,844,412 B2 | 12/2017 | Bogusky et al. | |
| 9,867,635 B2 | 1/2018 | Alvarez et al. | |
| 9,918,659 B2 | 3/2018 | Chopra et al. | |
| 9,918,681 B2 | 3/2018 | Wallace et al. | |
| 9,931,025 B1 | 4/2018 | Graetzel et al. | |
| 9,949,749 B2 | 4/2018 | Noonan et al. | |
| 9,955,986 B2 | 5/2018 | Shah | |
| 9,962,228 B2 | 5/2018 | Schuh et al. | |
| 9,980,785 B2 | 5/2018 | Schuh | |
| 9,993,313 B2 | 6/2018 | Schuh et al. | |
| 10,016,900 B1 | 7/2018 | Meyer et al. | |
| 10,022,192 B1 | 7/2018 | Ummalaneni | |
| 10,080,576 B2 | 9/2018 | Romo et al. | |
| 10,130,427 B2 | 11/2018 | Tanner et al. | |
| 10,145,747 B1 | 12/2018 | Lin et al. | |
| 10,149,720 B2 * | 12/2018 | Romo | A61B 1/0056 |
| 10,159,532 B1 | 12/2018 | Ummalaneni | |
| 10,299,870 B2 | 5/2019 | Connolly et al. | |
| 10,426,559 B2 | 10/2019 | Graetzel et al. | |
| 10,434,660 B2 | 10/2019 | Meyer et al. | |
| 10,639,114 B2 | 5/2020 | Schuh et al. | |
| 10,667,875 B2 | 6/2020 | DeFonzo et al. | |
| 10,743,751 B2 | 8/2020 | Andey et al. | |
| 10,751,140 B2 | 8/2020 | Wallace et al. | |
| 10,765,487 B2 | 9/2020 | Ho et al. | |
| 2001/0004676 A1 | 6/2001 | Ouchi | |
| 2003/0036748 A1 | 2/2003 | Cooper et al. | |
| 2003/0130564 A1 | 7/2003 | Martone et al. | |
| 2003/0158545 A1 | 8/2003 | Hovda et al. | |
| 2003/0163199 A1 | 8/2003 | Boehm et al. | |
| 2003/0195664 A1 | 10/2003 | Nowlin et al. | |
| 2004/0015122 A1 | 1/2004 | Zhang et al. | |
| 2004/0030349 A1 | 2/2004 | Boukhny | |
| 2004/0054322 A1 | 3/2004 | Vargas | |
| 2004/0059257 A1 * | 3/2004 | Gaber | A61M 25/0147 |
| | | | 600/585 |
| 2004/0072066 A1 | 4/2004 | Cho et al. | |
| 2004/0138525 A1 | 7/2004 | Saadat et al. | |
| 2004/0138529 A1 * | 7/2004 | Wiltshire | A61B 1/0055 |
| | | | 600/144 |
| 2004/0193013 A1 | 9/2004 | Iwasaka et al. | |
| 2004/0193146 A1 * | 9/2004 | Lee | A61B 17/062 |
| | | | 606/1 |
| 2004/0249246 A1 | 12/2004 | Campos | |
| 2005/0004515 A1 * | 1/2005 | Hart | A61B 17/3421 |
| | | | 604/95.04 |
| 2005/0070844 A1 | 3/2005 | Chow et al. | |
| 2005/0125005 A1 | 6/2005 | Fujikura | |
| 2005/0131279 A1 | 6/2005 | Boulais et al. | |
| 2005/0154262 A1 | 7/2005 | Banik et al. | |
| 2005/0159646 A1 | 7/2005 | Nordstrom et al. | |
| 2005/0165366 A1 | 7/2005 | Brustad et al. | |
| 2005/0197623 A1 | 9/2005 | Eeflang et al. | |
| 2005/0222581 A1 | 10/2005 | Fischer et al. | |
| 2005/0234293 A1 | 10/2005 | Yamamoto et al. | |
| 2005/0256452 A1 | 11/2005 | DeMarchi et al. | |
| 2005/0272975 A1 | 12/2005 | McWeeney et al. | |
| 2005/0273085 A1 * | 12/2005 | Hinman | A61B 1/0055 |
| | | | 606/1 |
| 2005/0288549 A1 | 12/2005 | Mathis | |
| 2006/0041188 A1 | 2/2006 | Dirusso et al. | |
| 2006/0111692 A1 | 5/2006 | Hlavka et al. | |
| 2006/0173243 A1 | 8/2006 | Watanabe | |
| 2006/0224184 A1 | 10/2006 | Stefanchik et al. | |
| 2006/0241368 A1 | 10/2006 | Fichtinger et al. | |
| 2006/0264708 A1 | 11/2006 | Horne | |
| 2006/0276827 A1 | 12/2006 | Mitelberg et al. | |
| 2006/0287769 A1 | 12/2006 | Yanagita et al. | |
| 2007/0032906 A1 | 2/2007 | Sutherland et al. | |
| 2007/0060879 A1 | 3/2007 | Weitzner et al. | |
| 2007/0112355 A1 | 5/2007 | Salahieh et al. | |
| 2007/0135733 A1 * | 6/2007 | Soukup | A61M 25/0136 |
| | | | 604/95.04 |
| 2007/0135763 A1 * | 6/2007 | Musbach | A61M 25/0054 |
| | | | 604/96.01 |
| 2007/0135803 A1 | 6/2007 | Belson | |
| 2007/0156019 A1 | 7/2007 | Larkin et al. | |
| 2007/0270645 A1 | 11/2007 | Ikeda | |
| 2007/0270679 A1 | 11/2007 | Nguyen et al. | |
| 2007/0282167 A1 | 12/2007 | Barenboym et al. | |
| 2007/0287886 A1 | 12/2007 | Saadat | |
| 2007/0299427 A1 | 12/2007 | Yeung et al. | |
| 2008/0039255 A1 | 2/2008 | Jinno et al. | |
| 2008/0051629 A1 | 2/2008 | Sugiyama et al. | |

(56)          References Cited

U.S. PATENT DOCUMENTS

| | | | |
|---|---|---|---|
| 2008/0051802 A1* | 2/2008 | Schostek | A61B 1/00135 |
| | | | 600/101 |
| 2008/0064921 A1 | 3/2008 | Larkin et al. | |
| 2008/0065103 A1 | 3/2008 | Cooper et al. | |
| 2008/0065109 A1 | 3/2008 | Larkin | |
| 2008/0086047 A1* | 4/2008 | McDaniel | A61M 25/0136 |
| | | | 600/374 |
| 2008/0097293 A1* | 4/2008 | Chin | A61M 25/0051 |
| | | | 604/524 |
| 2008/0108869 A1 | 5/2008 | Sanders et al. | |
| 2008/0114341 A1 | 5/2008 | Thyzel | |
| 2008/0139887 A1 | 6/2008 | Fitzpatrick | |
| 2008/0146874 A1 | 6/2008 | Chen | |
| 2008/0147089 A1 | 6/2008 | Loh et al. | |
| 2008/0177285 A1 | 7/2008 | Brock et al. | |
| 2008/0187101 A1 | 8/2008 | Gertner | |
| 2008/0208001 A1* | 8/2008 | Hadani | A61B 1/00071 |
| | | | 600/128 |
| 2008/0212082 A1 | 9/2008 | Froggatt et al. | |
| 2008/0218770 A1 | 9/2008 | Moll et al. | |
| 2008/0228104 A1 | 9/2008 | Uber et al. | |
| 2008/0234545 A1* | 9/2008 | Breedveld | A61B 17/29 |
| | | | 600/104 |
| 2008/0249483 A1 | 10/2008 | Slenker et al. | |
| 2009/0099420 A1 | 4/2009 | Woodley et al. | |
| 2009/0137952 A1 | 5/2009 | Ramamurthy et al. | |
| 2009/0163851 A1 | 6/2009 | Holloway et al. | |
| 2009/0171271 A1 | 7/2009 | Webster et al. | |
| 2009/0192495 A1* | 7/2009 | Ostrovsky | A61M 25/0138 |
| | | | 604/528 |
| 2009/0247880 A1 | 10/2009 | Naruse et al. | |
| 2009/0248041 A1 | 10/2009 | Williams et al. | |
| 2009/0248043 A1 | 10/2009 | Tierney et al. | |
| 2009/0254083 A1 | 10/2009 | Wallace et al. | |
| 2009/0262109 A1 | 10/2009 | Markowitz et al. | |
| 2009/0264878 A1 | 10/2009 | Carmel et al. | |
| 2009/0268015 A1 | 10/2009 | Scott et al. | |
| 2009/0299344 A1 | 12/2009 | Lee et al. | |
| 2009/0306587 A1 | 12/2009 | Milijasevic et al. | |
| 2009/0312768 A1 | 12/2009 | Hawkins et al. | |
| 2009/0326322 A1 | 12/2009 | Diolaiti | |
| 2010/0030023 A1 | 2/2010 | Yoshie | |
| 2010/0036294 A1 | 2/2010 | Mantell et al. | |
| 2010/0069962 A1 | 3/2010 | Harms et al. | |
| 2010/0073150 A1 | 3/2010 | Olson et al. | |
| 2010/0114115 A1 | 5/2010 | Schlesinger et al. | |
| 2010/0130823 A1* | 5/2010 | Ando | A61B 1/00078 |
| | | | 600/141 |
| 2010/0168918 A1 | 7/2010 | Zhao et al. | |
| 2010/0217184 A1 | 8/2010 | Koblish et al. | |
| 2010/0228191 A1 | 9/2010 | Alvarez et al. | |
| 2010/0249497 A1 | 9/2010 | Peine et al. | |
| 2010/0249506 A1 | 9/2010 | Prisco | |
| 2010/0312056 A1* | 12/2010 | Galperin | A61B 1/0051 |
| | | | 600/141 |
| 2010/0331856 A1 | 12/2010 | Carlson et al. | |
| 2011/0004157 A1* | 1/2011 | Dewaele | A61M 25/0141 |
| | | | 604/95.01 |
| 2011/0009779 A1 | 1/2011 | Romano et al. | |
| 2011/0009863 A1 | 1/2011 | Marczyk et al. | |
| 2011/0028887 A1 | 2/2011 | Fischer et al. | |
| 2011/0040404 A1 | 2/2011 | Diolaiti et al. | |
| 2011/0046411 A1 | 2/2011 | Öhrlein et al. | |
| 2011/0046441 A1* | 2/2011 | Wiltshire | A61B 1/313 |
| | | | 600/104 |
| 2011/0071508 A1 | 3/2011 | Duval et al. | |
| 2011/0077681 A1 | 3/2011 | Nagano et al. | |
| 2011/0098533 A1 | 4/2011 | Onoda et al. | |
| 2011/0106102 A1 | 5/2011 | Balicki et al. | |
| 2011/0130718 A1 | 6/2011 | Kidd et al. | |
| 2011/0148442 A1 | 6/2011 | Berner et al. | |
| 2011/0152880 A1 | 6/2011 | Alvarez et al. | |
| 2011/0237888 A1 | 9/2011 | Matsushita | |
| 2011/0245844 A1 | 10/2011 | Jinno | |
| 2011/0261183 A1 | 10/2011 | Ma et al. | |
| 2011/0270084 A1 | 11/2011 | Choi et al. | |
| 2011/0295242 A1* | 12/2011 | Spivey | A61B 17/07207 |
| | | | 606/1 |
| 2011/0306836 A1 | 12/2011 | Ohline et al. | |
| 2012/0071894 A1 | 3/2012 | Tanner et al. | |
| 2012/0071895 A1 | 3/2012 | Stahler et al. | |
| 2012/0123327 A1 | 5/2012 | Miller | |
| 2012/0136419 A1 | 5/2012 | Zarembo et al. | |
| 2012/0138586 A1 | 6/2012 | Webster et al. | |
| 2012/0143226 A1 | 6/2012 | Belson et al. | |
| 2012/0190976 A1 | 7/2012 | Kleinstreuer | |
| 2012/0191107 A1 | 7/2012 | Tanner et al. | |
| 2012/0239012 A1 | 9/2012 | Laurent et al. | |
| 2012/0259244 A1 | 10/2012 | Roberts et al. | |
| 2012/0283747 A1 | 11/2012 | Popovic | |
| 2012/0289777 A1 | 11/2012 | Chopra et al. | |
| 2013/0018400 A1 | 1/2013 | Milton et al. | |
| 2013/0030519 A1 | 1/2013 | Tran et al. | |
| 2013/0035537 A1 | 2/2013 | Wallace et al. | |
| 2013/0072787 A1 | 3/2013 | Wallace et al. | |
| 2013/0090552 A1 | 4/2013 | Ramamurthy et al. | |
| 2013/0109957 A1 | 5/2013 | Hooft et al. | |
| 2013/0144116 A1 | 6/2013 | Cooper et al. | |
| 2013/0165854 A1 | 6/2013 | Sandhu et al. | |
| 2013/0165908 A1* | 6/2013 | Purdy | A61B 1/0052 |
| | | | 606/1 |
| 2013/0204124 A1 | 8/2013 | Duindam et al. | |
| 2013/0226151 A1 | 8/2013 | Suehara | |
| 2013/0303892 A1 | 11/2013 | Zhao et al. | |
| 2013/0304091 A1 | 11/2013 | Straehnz et al. | |
| 2013/0317276 A1 | 11/2013 | D'Andrea | |
| 2013/0317519 A1 | 11/2013 | Romo et al. | |
| 2013/0345519 A1 | 12/2013 | Piskun et al. | |
| 2014/0012276 A1 | 1/2014 | Alvarez | |
| 2014/0012288 A1 | 1/2014 | Darisse et al. | |
| 2014/0046313 A1 | 2/2014 | Pederson et al. | |
| 2014/0069437 A1 | 3/2014 | Reis et al. | |
| 2014/0142591 A1 | 5/2014 | Alvarez et al. | |
| 2014/0200402 A1 | 7/2014 | Snoke et al. | |
| 2014/0235943 A1 | 8/2014 | Paris et al. | |
| 2014/0276391 A1 | 9/2014 | Yu | |
| 2014/0276594 A1 | 9/2014 | Tanner et al. | |
| 2014/0309649 A1 | 10/2014 | Alvarez et al. | |
| 2014/0316397 A1 | 10/2014 | Brown | |
| 2014/0343416 A1 | 11/2014 | Panescu et al. | |
| 2014/0357984 A1 | 12/2014 | Wallace et al. | |
| 2014/0364870 A1 | 12/2014 | Alvarez et al. | |
| 2014/0379000 A1 | 12/2014 | Romo et al. | |
| 2015/0025539 A1 | 1/2015 | Alvarez et al. | |
| 2015/0031950 A1 | 1/2015 | Drontle et al. | |
| 2015/0051592 A1 | 2/2015 | Kintz | |
| 2015/0101442 A1 | 4/2015 | Romo | |
| 2015/0119637 A1 | 4/2015 | Alvarez et al. | |
| 2015/0119638 A1 | 4/2015 | Yu et al. | |
| 2015/0164594 A1 | 6/2015 | Romo et al. | |
| 2015/0164595 A1 | 6/2015 | Bogusky et al. | |
| 2015/0164596 A1 | 6/2015 | Romo et al. | |
| 2015/0255782 A1 | 9/2015 | Kim et al. | |
| 2015/0335480 A1 | 11/2015 | Alvarez et al. | |
| 2015/0367508 A1* | 12/2015 | Hatakeyama | A61B 34/30 |
| | | | 74/490.04 |
| 2016/0000414 A1 | 1/2016 | Brown et al. | |
| 2016/0001038 A1 | 1/2016 | Romo et al. | |
| 2016/0007881 A1 | 1/2016 | Wong et al. | |
| 2016/0067450 A1 | 3/2016 | Kowshik | |
| 2016/0151122 A1 | 6/2016 | Alvarez et al. | |
| 2016/0167223 A1* | 6/2016 | Zubiate | B25J 9/105 |
| | | | 901/21 |
| 2016/0183841 A1 | 6/2016 | Duindam et al. | |
| 2016/0227982 A1 | 8/2016 | Takahashi et al. | |
| 2016/0270865 A1 | 9/2016 | Landey et al. | |
| 2016/0287279 A1 | 10/2016 | Bovay et al. | |
| 2016/0287346 A1 | 10/2016 | Hyodo et al. | |
| 2016/0296294 A1 | 10/2016 | Moll et al. | |
| 2016/0310702 A1* | 10/2016 | Cabiri | A61M 25/0138 |
| 2016/0338783 A1 | 11/2016 | Romo et al. | |
| 2016/0338785 A1 | 11/2016 | Kokish et al. | |
| 2016/0346049 A1 | 12/2016 | Allen et al. | |

(56) References Cited

U.S. PATENT DOCUMENTS

| | | |
|---|---|---|
| 2016/0372743 A1 | 12/2016 | Cho et al. |
| 2016/0374541 A1 | 12/2016 | Agrawal et al. |
| 2016/0374590 A1 | 12/2016 | Wong et al. |
| 2017/0007337 A1 | 1/2017 | Dan |
| 2017/0065364 A1 | 3/2017 | Schuh et al. |
| 2017/0065365 A1 | 3/2017 | Schuh |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0202627 A1 | 7/2017 | Sramek et al. |
| 2017/0209073 A1 | 7/2017 | Sramek et al. |
| 2017/0281218 A1 | 10/2017 | Timm |
| 2017/0290631 A1 | 10/2017 | Lee et al. |
| 2017/0333679 A1 | 11/2017 | Jiang |
| 2017/0340396 A1 | 11/2017 | Romo et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0042452 A1* | 2/2018 | Okada ..................... A61B 1/01 |
| 2018/0055583 A1 | 3/2018 | Schuh et al. |
| 2018/0055589 A1 | 3/2018 | Joseph et al. |
| 2018/0177383 A1 | 6/2018 | Noonan et al. |
| 2018/0177517 A1* | 6/2018 | Lippert .............. A61B 17/3207 |
| 2018/0177556 A1 | 6/2018 | Noonan |
| 2018/0177561 A1 | 6/2018 | Mintz et al. |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0289243 A1 | 10/2018 | Landey et al. |
| 2018/0289431 A1 | 10/2018 | Draper et al. |
| 2018/0325499 A1 | 11/2018 | Landey et al. |
| 2018/0333044 A1 | 11/2018 | Jenkins |
| 2018/0360435 A1* | 12/2018 | Romo .................... A61B 34/30 |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0083183 A1 | 3/2019 | Moll et al. |
| 2019/0105110 A1 | 4/2019 | Tanner et al. |
| 2019/0105776 A1 | 4/2019 | Ho et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298458 A1 | 10/2019 | Srinivasan et al. |
| 2019/0298460 A1 | 10/2019 | Al-Jadda et al. |
| 2019/0298465 A1 | 10/2019 | Chin et al. |
| 2019/0307987 A1 | 10/2019 | Yu |
| 2019/0336238 A1 | 11/2019 | Yu et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000533 A1 | 1/2020 | Schuh et al. |
| 2020/0022767 A1 | 1/2020 | Hill et al. |
| 2020/0038128 A1 | 2/2020 | Joseph et al. |
| 2020/0039086 A1 | 2/2020 | Meyer et al. |
| 2020/0046434 A1 | 2/2020 | Graetzel et al. |
| 2020/0046942 A1 | 2/2020 | Alvarez et al. |
| 2020/0054408 A1 | 2/2020 | Schuh et al. |
| 2020/0060516 A1 | 2/2020 | Baez, Jr. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0188043 A1 | 6/2020 | Yu et al. |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0261172 A1 | 8/2020 | Romo et al. |
| 2020/0268459 A1 | 8/2020 | Noonan |
| 2020/0268460 A1 | 8/2020 | Tse et al. |

FOREIGN PATENT DOCUMENTS

| | | | |
|---|---|---|---|
| CN | 1846181 A | 10/2006 | |
| CN | 1857877 A | 11/2006 | |
| CN | 102088920 A | 6/2011 | |
| CN | 102316817 A | 1/2012 | |
| CN | 102458295 A | 5/2012 | |
| CN | 102711586 A | 10/2012 | |
| CN | 102973317 A | 3/2013 | |
| CN | 103767659 A | 5/2014 | |
| CN | 103930063 A | 7/2014 | |
| EP | 0543539 A1 | 5/1993 | |
| EP | 0776739 A2 | 6/1997 | |
| EP | 0904796 A2 | 3/1999 | |
| EP | 1442720 A1 | 8/2004 | |
| JP | h09224951 B | 9/1997 | |
| JP | 2007511247 A | 5/2007 | |
| JP | 2010046384 A | 3/2010 | |
| JP | 2011015992 A | 1/2011 | |
| JP | 2012105793 A | 6/2012 | |
| KR | 10-2012-0028100 A | 3/2012 | |
| WO | 9214411 A1 | 9/1992 | |
| WO | 0067640 A2 | 11/2000 | |
| WO | 0105849 A1 | 1/2001 | |
| WO | 02074178 A2 | 9/2002 | |
| WO | 03096871 A2 | 11/2003 | |
| WO | 2004039273 A2 | 5/2004 | |
| WO | 2004103430 A2 | 12/2004 | |
| WO | 2004105849 A1 | 12/2004 | |
| WO | 2004114037 A2 | 12/2004 | |
| WO | 2005032637 A2 | 4/2005 | |
| WO | 2005081202 A2 | 9/2005 | |
| WO | 2007146987 A2 | 12/2007 | |
| WO | 2008097540 A2 | 8/2008 | |
| WO | 2009092059 A2 | 7/2009 | |
| WO | 2009097461 A1 | 8/2009 | |
| WO | 2009126309 A2 | 10/2009 | |
| WO | WO-2010081187 A1 * | 7/2010 | ........ A61M 25/0054 |
| WO | 2010088187 A1 | 8/2010 | |
| WO | 2010093153 A2 | 8/2010 | |
| WO | 2010133733 A1 | 11/2010 | |
| WO | 2011100110 A1 | 8/2011 | |
| WO | 2011161218 A1 | 12/2011 | |
| WO | 2013071071 A1 | 5/2013 | |
| WO | 2013107468 A1 | 7/2013 | |

(56)        References Cited

FOREIGN PATENT DOCUMENTS

| WO | 2014133180 A1 | 9/2014 |
| WO | 2014138729 A1 | 9/2014 |
| WO | 2016037133 A1 | 3/2016 |

OTHER PUBLICATIONS

Balicki, et al. Single fiber optical coherence tomography microsurgical instruments for computer androbot-assisted retinal surgery. Medical Image Computing and Computer-Assisted Intervention. MICCAI 2009. SprinQer Berlin Heidelberg, 2009. 108-115, 8 pages.

Ehlers, et al. Integration of a spectral domain optical coherence tomography system into a surgical microscope for Intraoperative imaging. Investigative Ophthalmology and Visual Science 52.6. 2011; 3153-3159, 7 pages.

European search report and search opinion dated Jul. 2, 2015 for EP Application No. 12856685.8, 5 pages.

European Search Report and Search Opinion, dated Sep. 16, 2016, for EP Application No. 14760802, 5 pages.

Final Rejection for U.S. Appl. No. 14/201,610, dated Feb. 3, 2017, 10 pages.

Final Rejection for U.S. Appl. No. 16/115,389, dated Oct. 24, 2022, 10 pages.

Hubschman. Robotic Eye Surgery: Past, Present, and Future. Journal of Computer Science and Systems Biology. 2012. 4 pages.

International search report and written opinion dated Nov. 7, 2014 for PCT Application No. PCT/US2014/041990, 7 pages.

International search report and written opinion dated Mar. 29, 2013 for PCT/US2012/069540, 7 pages.

International Search Report and Written Opinion, dated Dec. 4, 2015, for PCT Application No. PCT/US2015/048688, 7 pages.

International Search Report and Written Opinion, dated Jan. 27, 2015, for PCT Application No. PCT/ US2014/062284, 7 pages.

International search report dated Jun. 16, 2014 for PCT/US2014/ 022424, 3 pages.

Non-Final Rejection for U.S. Appl. No. 16/115,389, dated Mar. 19, 2022, 18 pages.

Non-Final Rejection for U.S. Appl. No. 14/201,601, dated Aug. 4, 2017, 7 pages.

Non-Final Rejection for U.S. Appl. No. 14/201,610, dated Nov. 8, 2017, 9 pages.

Non-Final Rejection for U.S. Appl. No. 14/201,610, dated Sep. 2, 2016, 8 pages.

Notice of Allowance for U.S. Appl. No. 14/201,610, dated Aug. 15, 2018, 5 pages.

Notice of Allowance for U.S. Appl. No. 14/201,610, dated May 1, 2018, 8 pages.

Notice of Allowance for U.S. Appl. No. 16/115,389 dated Mar. 29, 2023, 9 pages.

Office action dated Jun. 11, 2015 for U.S. Appl. No. 14/158,548, 10 pages.

Office Action dated Jul. 10, 2017 for U.S. Appl. No. 14/479,095, 11 pages.

Office action dated May 21, 2015 for U.S. Appl. No. 13/711,440, 14 pages.

Verdaasdonk et al., Jan. 23, 2012, Effect of Microsecond Pulse Length and Tip Shape on Explosive Bubble Formation of 2.78 μm Er,Cr;YSGG and 2.94 μm Er:YAG laser, Proceedings of SPIE, vol. 8221, 12, 1 pages.

* cited by examiner

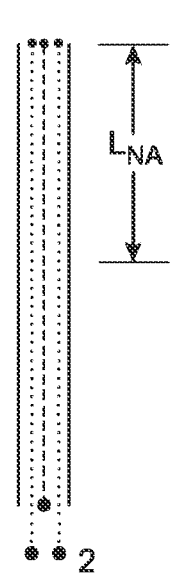
FIG. 1A
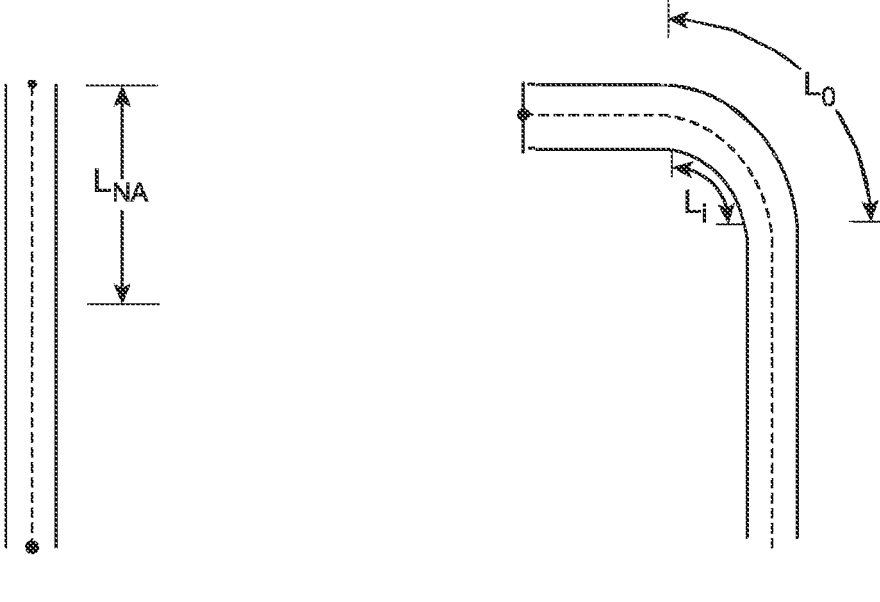
FIG. 1B
FIG. 2A
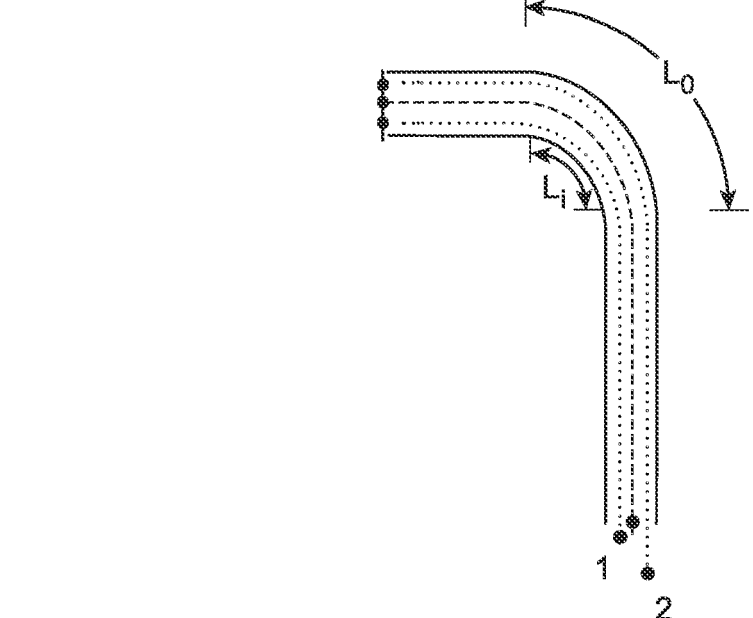
FIG. 2B

FIG. 8A                              FIG. 8B

METHOD, APPARATUS, AND SYSTEM FOR FACILITATING BENDING OF AN INSTRUMENT IN A SURGICAL OR MEDICAL ROBOTIC ENVIRONMENT

CROSS-REFERENCE TO RELATED APPLICATION

This application is a continuation of U.S. patent application Ser. No. 16/115,389, filed Aug. 28, 2018, which is a continuation of U.S. application Ser. No. 14/201,610, filed Mar. 7, 2014, now U.S. Pat. No. 10,149,720, which claims the benefit of U.S. Provisional Application No. 61/774,901, filed Mar. 8, 2013, each of which is hereby incorporated by reference in its entirety.

BACKGROUND

Field

The field of the present application pertains to medical devices. More particularly, the field of the invention pertains to an apparatus, system, and method for performing surgery.

Description of the Related Art

Robotic surgery has many benefits to improve patient recovery time and allows precise control of medical and surgical application instruments. In robotics, an end effector is the device at the end of a robotic arm, designed to interact with the environment. The exact nature of this device depends on the application of the robot. For example, several examples of end effectors could include a set of forceps, a pair of scissors, a laser, a camera, a cautery tool, a needle, or any other instrument tip that would benefit from being able to be repositioned.

As previously discussed, which originates from serial robotic manipulators, the end effector means the last link (or end) of the robot. At this endpoint the tools are attached. In a wider sense, an end effector can be seen as the part of a robot that interacts with the work environment.

Many articulating devices use bending sections comprising many small moving parts for creating an assembly. Typically, the assemblies are difficult to manufacture in smaller geometries since the individual components become difficult to fabricate.

Another challenge with existing solutions is accommodating the ancillary components for the end effector; which may include pull wire, electrical wires, fluidic lines, and optical fibers. The location of these components within the bending section impacts performance and stability of the bending section. All beams have an imaginary line within the body what will remain the same length when straight or bent, this line is termed the Neutral Axis $L_{NA}$ of the structure. The neutral axis $L_{NA}$ region does not experience any strain or stress. Typically, material that falls on either side of this line will experience strain and will either be extended or compressed. The inside of the bend will compress $L_i$ and the outside of the bend will extend $L_o$. See FIG. 1 for illustrations of the neutral axis along with its relationship to the inner and outer bend surfaces.

For example, if the ancillary components are placed outside of the neutral axis region, they will slide in and out of the bending section if they are able to float relative to the bending section. Otherwise, the components will buckle or stretch due to the axial forces being imposed. FIG. 2 depicts an illustration of the relationship of components placed away from the components neutral axis.

Existing solutions for bending sections are created for small articulable instruments that is manufactured from thin walled tube. For example, intricate patterns are cut into the tubing in order to create reliefs that yield a preferential bending direction. However, if a large deflection is required; much of the tubing material will need to be removed in order to allow for such bending. Consequently, a thin walled tube with lots of its material eliminated inevitably loses much of the structure and ability to remain mechanically stable.

Therefore, it would be advantageous to have a method and apparatus for facilitating the bending of an instrument with large degrees of articulation while maintaining a sufficient amount of stiffness in order to provide stability at the end effector, all while ensuring ease of manufacturing.

SUMMARY

Embodiments described herein are directed to a method, apparatus, and system for bending of an instrument with large degrees of articulation while maintaining ease of manufacturing.

In other embodiments, methods and apparatus for creating an articulating segment by starting with a solid rod instead of a tube. First, material is removed from the sides of the rod for enabling a bend. In one embodiment, the rod has material removed from the cross section in order to accommodate an actuation wire.

In other embodiments, the cross section accommodates ancillary components pertaining to the end effector.

One embodiment provides placing the path of the ancillary components close to the neutral axis of the bending section. Consequently, this reduces interactions between the articulation of the bending section and the ancillary components. Furthermore, resulting in a more predictable bend and end effector behavior. For example and not by way of limitation, removing material from the cross section to accommodate the articulation pull wire and the ancillary components permits manipulation of bending stiffness and the amount of opposing forces it is able to resolve during a medical procedure.

In one embodiment, the component is manufactured from a superplastic material that will be discussed later, such as, but not limited to Nitinol and other similar materials. The stiffness of the structure was manipulated via the design of the cross sectional profile in order to ensure the structure provides enough stability throughout the complete range of motion. The structure achieves a significant bend by imposing a moment on the structure and will recover to the original position when the moment is removed from the structure.

This actuation would simply require one pull wire at the tip, which would need to be pulled in order to generate a moment and relaxed to relieve the moment.

In an alternative embodiment, the component is manufactured from a superplastic material, but the cross section allows a different inner profile by incorporating the relief on the profile, the device lends itself to be manufactured using the wire EDM (Electric Discharge Machining) process without having to initially create a clearance hole.

BRIEF DESCRIPTION OF THE DRAWINGS

FIGS. 1A-1B are views to facilitate description of a neutral axis;

FIGS. 2A-2B are views to facilitate description of a neutral axis;

FIGS. 8A-8E depict an apparatus for a bending flexure according to a second embodiment of the present invention;

DETAILED DESCRIPTION

Figure 3A:
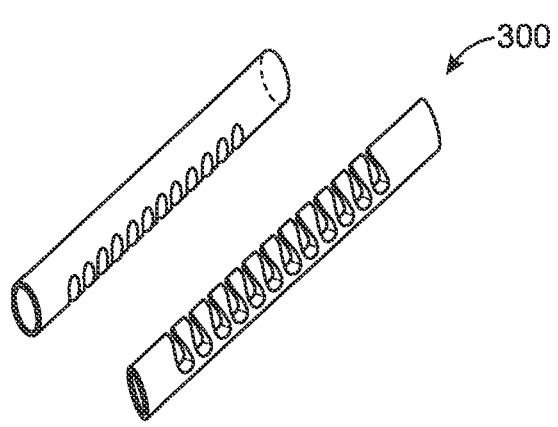
FIGS. 3A-3D depict an apparatus for a bending flexure according to a first embodiment of the present invention.

Although certain preferred embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

The embodiments described herein are directed to an apparatus for a distal bending section of minimally invasive surgical instrument having a large degree of articulation and providing sufficient rigidity to resolve the required forces during remote surgical procedures. Other embodiments provide methods of using the distal bending section and methods for making it.

One embodiment provides placing the path of the ancillary components close to the neutral axis of the bending section. Consequently, this reduces interactions between the articulation of the bending section and the ancillary components. Furthermore, embodiments of the present invention provide a more predictable bend and end effector behavior. For example and not by way of limitation, removing material from the cross section accommodates the articulation pull wire and the ancillary components, hence, the bending stiffness can be manipulated in order to achieve a desired characteristic.

In one embodiment, the component is manufactured from a superplastic material. In one embodiment, the material is Nitinol and with superelastic phase at room and/or body temperature. Also, other embodiments include use of any super elastic alloy. In yet another embodiment, the moment of inertia was tuned such that the structure achieves a significant bend by generating a moment on the structure and recovers to the original position when the moment is removed. This actuation would simply require one pull wire at the tip, which would need to be pulled in order to generate a moment and relaxed to relieve the moment.

In an alternative embodiment, the component is manufactured from a superplastic material, but the cross section allows a different inner profile by incorporating the relief on the profile, the device lends itself to be manufactured using the wire EDM (Electric Discharge Machining) process without having to initially create a clearance hole.

Figure 3B:
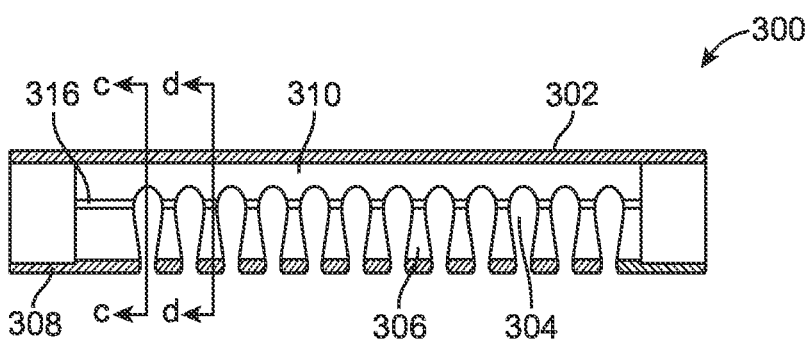

Referring to FIG. 3A, finished bending section 300 in accordance to an embodiment of the present invention is depicted. FIG. 3B is a longitudinal cross-section through the axis of bending section 300, FIG. 3C shows an axial cross-section of bending section 300 along line C (c-c) of FIG. 3B, and FIG. 3D shows an axial cross-section of bending section 300 along line D (d-d) of FIG. 3B.

Referring to FIG. 3B, material is removed along the top portion of a rod to create void 302, preferably along the length of the bending section. As discussed below, this void is created to assist in removal of material in the road to create the additional features of this preferred embodiment. Material is also removed from teardrop sections 304, where adjacent to teardrop section 304 material is left in place forming leaves 306. A tendon (not shown) extends through void 308 (described below) is attached at the distal end of bending section 300. When tension is applied to the tendon bending section will bend downward, as shown in the figure, and teardrop voids 304 permit leaves 306 to move inward, and a bend is realized along solid spine 310. The skilled artisan will appreciate the selection of shapes for the teardrop voids and leaves is a matter of design choice, as well as the amount of material left to form spine 310.

Figure 3C:
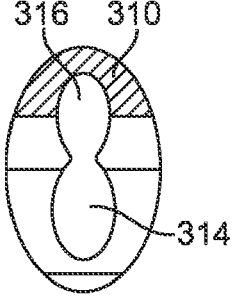
Figure 3D:
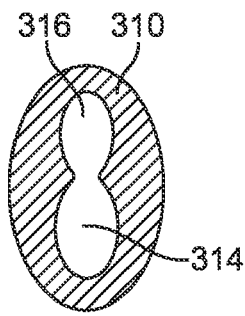

Referring now to FIG. 3C, non-cylindrical channel [312] is formed down the length of the solid rod. Preferably the outer circumference of the rod, and therefore the bending section, has an approximately cylindrical shape, similar to that of a drawn hypotube. Prior art bending sections have material cut from a hypotube, and therefore have a cylindrical inner diameter as well, which results is a uniform sidewall thickness along the length of the prior art bending section. When the outer diameter of the bending section is small, the hypotube walls do not provide sufficient strength and rigidity when large degree articulations are required and where a surgical tool at the distal end requires this rigidity to perform desired procedures. Embodiments of the present invention provide a non cylindrical channel through the bending section, which permits distributing material off-axis (i.e., non-uniform wall thickness) to provide structural rigidity to the bending section, provides a pathway 314 for the tendon off-axis and a pathway 316 proximate to the neutral axis for auxiliary cables (not shown), such as tool actuating or articulating cables.

Figures 4A, 4B:
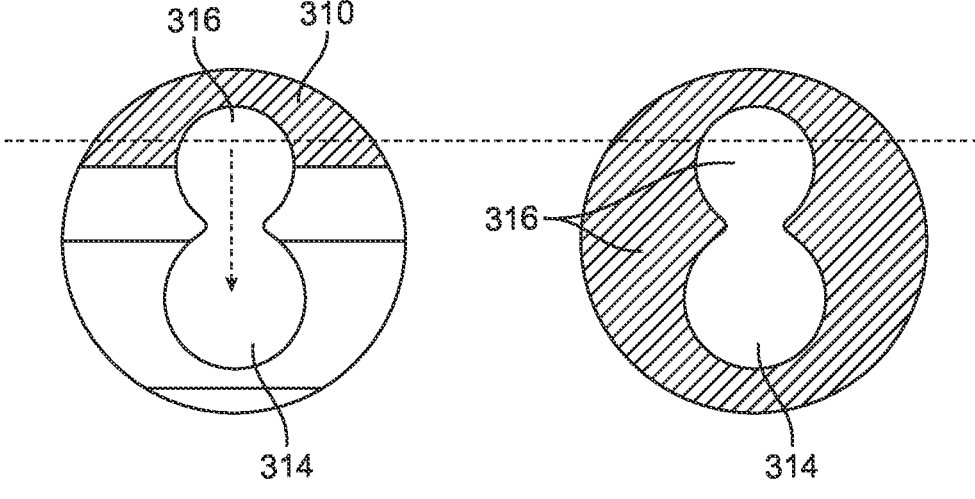
FIGS. 4A-4B are cross section side views of FIG. 3.
Figure 5:
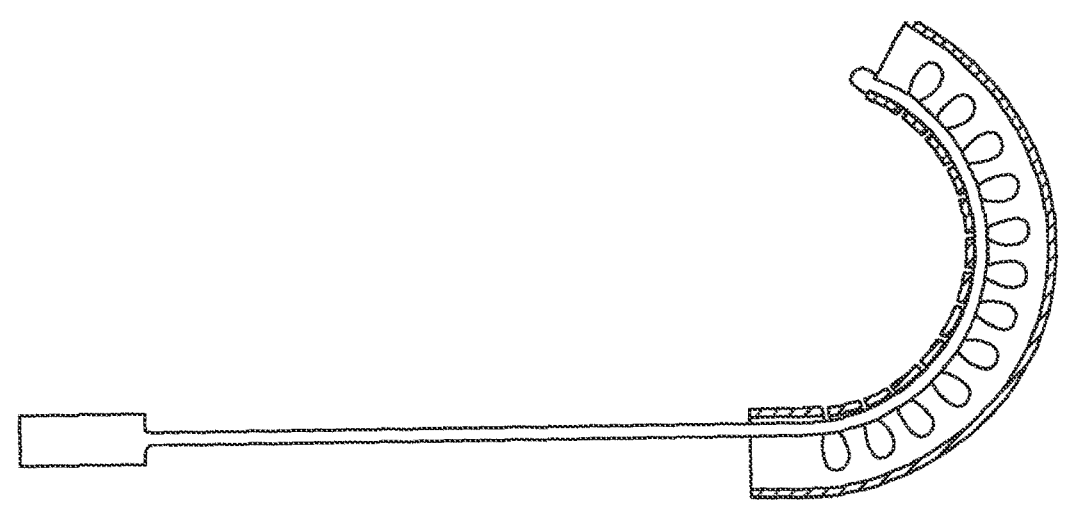
FIG. 5 is a view of a modeling representation of FIG. 3 according to a finite element analysis (FEA)

One embodiment provides for placing the path of the ancillary components as close to the neutral axis of the bending section. Consequently, this reduces interactions between the articulation of the bending section and the ancillary components. Furthermore, this embodiment provides a more predictable bend and end effector behavior. For example, removing enough material from the cross section to accommodate the articulation pull wire and the ancillary components, hence, the bending stiffness can be manipulated in order to achieve a desired characteristic. FIG. 4 is a cross section the same as shown in FIG. 3C. The location of the cross section locations relative to the structure are illustrated in FIG. 5. Section c-c demonstrates the cross section of the region 310 that will experience the bend and will contribute to the deflection of the structure. Section d-d demonstrates the region of the structure that provides a chassis 316, similar to a ribcage, to supports and house the components that are required to articulate the structure and manipulate the end effector. In this Figure, the hatched diagonal sections (referred to as hatched regions) depict a solid cross section. For example, section c-c has a solid cross section on the top portion. In contrast, section d-d has a solid cross section around the entire channel.

A dashed line near the top of the figure depicts the neutral axis of the apparatus. Also, a dashed arrow depicts the direction of the preferential bending away from the neutral axis in a downward direction.

Both section views of section c-c and d-d depict a dual oval shaped key opening, or lumen, to accommodate ancillary components (not shown) and an articulation wire (not shown). In some embodiments, the ancillary components could include any or all of the following:

Pull wires for generating actuation at the end effector;
Fibers for Illumination, laser, vision;
Pneumatics and/or hydraulics;
Electrical wires;
Open lumen for a working channel (open architecture device, end effector is passed through working channel and is interchangeable); and
A telescoping tube that supports the end effector.

In one embodiment, the top opening, or lumen, accommodates the ancillary components and the bottom opening accommodates the articulating wire that controls the bending of the apparatus. However, the skilled artisan appreciates different lumen configurations and placements based at least in part on the medical, surgical, or other application of the bending apparatus may be used without deviating from the present invention.

FIG. 5 is a view of a modeling representation of FIG. 3 according to a finite element analysis (FEA) which shows the interaction between the articulation wire (not shown and the flexure.

Figure 6:
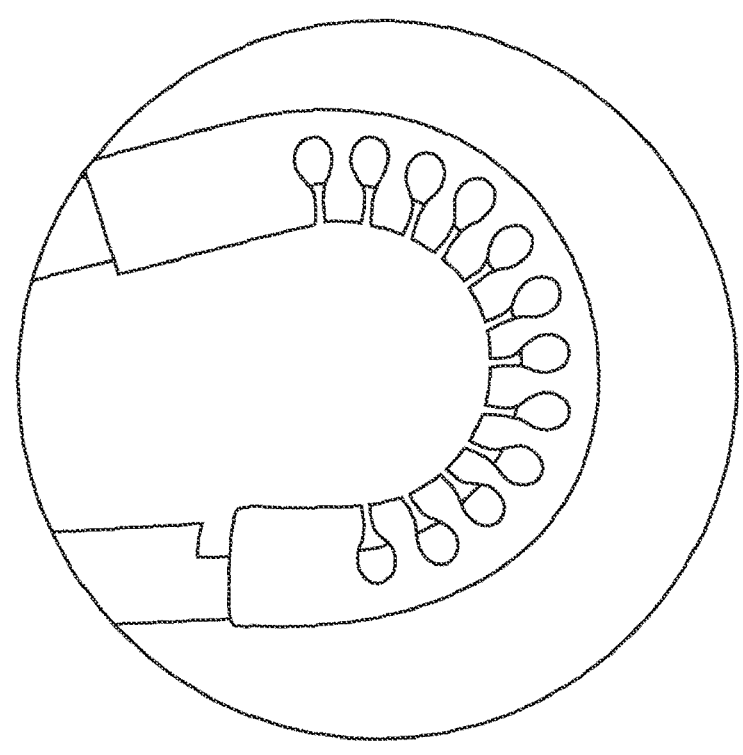
FIG. 6 is a view depicted an articulated position of the first embodiment depicted in FIG. 3.

FIG. 6 is a view depicting an articulated position of the embodiment depicted in FIGS. 3-4. This photograph was captured under a microscope and exemplifies the uniform bending of the structure. In one embodiment, the degree of articulation is based at least in part on the amount of reliefs/voids along the length of the structure. In this embodiment, one aspect of the relief also allows the structure a hard stop (a feedback of hitting a barrier) when the leaves come in contact. Consequently, embodiments of the present invention help to prevent over articulation and potential damage to the structure.

Figures 7A, 7B:
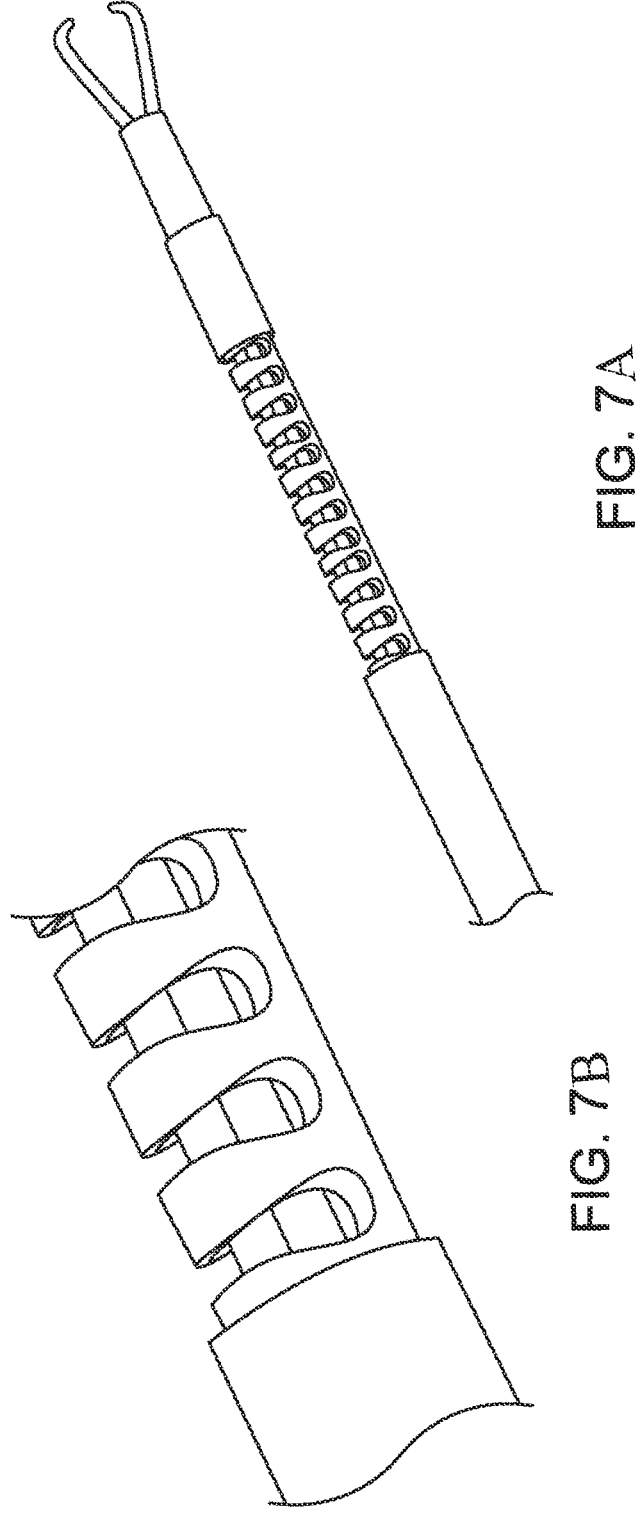
FIGS. 7A-7B are isometric views of an assembly, wherein the flexure subject matter is incorporated into an end effector, according to one embodiment of the present invention.
Figure 8C:
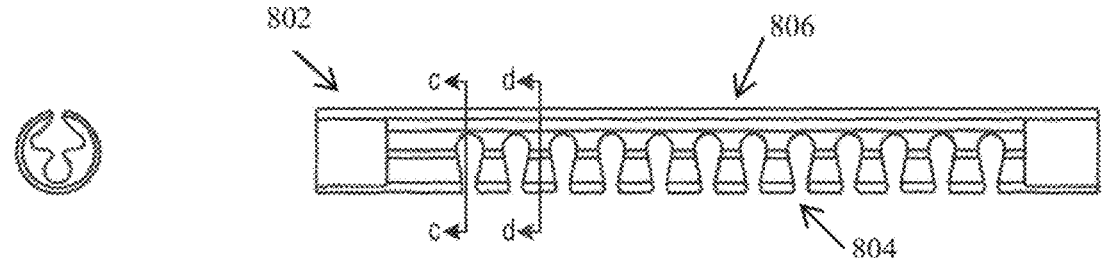
Figure 8C:
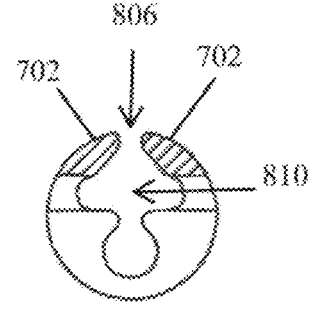
Figure 8D:
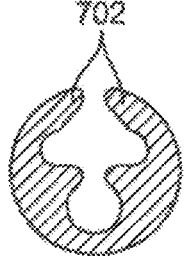
Figure 8E:
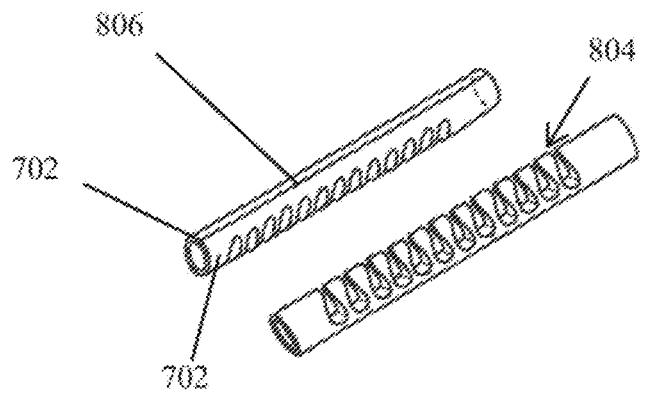

FIGS. 7A-7B are isometric views of an assembly, wherein the flexure subject matter is incorporated into an end effector, according to one embodiment of the claimed subject matter in the present invention;

FIGS. 8A-8E depict an apparatus for a bending flexure according to another embodiment of the present invention. The apparatus shown in FIGS. 8A-8E includes a body 802 with a teardrop section 804. The body 802 further includes struts 702 opposite of the teardrop section 804 that are separated by a slot 806 that defines a break out "gap." The skilled artisan will appreciate the shape of a non-cylindrical channel 810 through the body 802 can be varied to achieve desired bending and rigidity properties of the bending section. The cross section of the design depicted in FIGS. 8C-8D (also shown in FIGS. 9A-9B), permits the inner profile to break out. By incorporating this relief on the profile, the device lends itself to be manufactured using the wire EDM process without having to initially create a clearance hole.

Figures 9A, 9B:
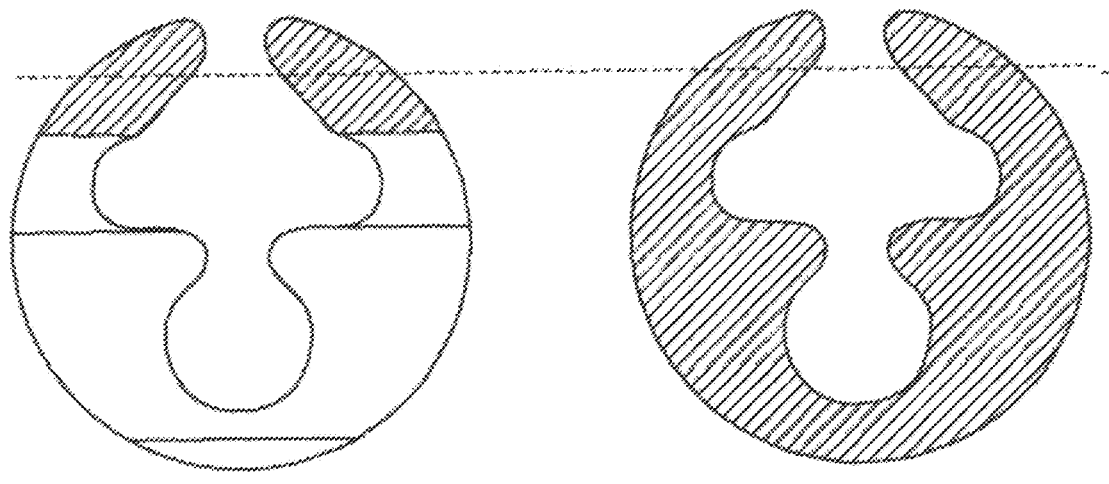
FIGS. 9A-9B are cross-section side views of FIG. 8B along lines c-c and d-d.

FIGS. 9A-9B are cross section side views of FIG. 8B. The two struts 702 on flexure #2 (FIG. 8D) tend to bend about the neutral axis, but also slightly into the center of the cross section. This bending characteristic will result in the break out "gap" to start to close as the flexure is articulated, and will eventually close completely during large articulations.

Also, in this second embodiment, an opening allows for lateral insertion of ancillary components. The concept of having a break out on the inner profile also has a benefit during the assembly process. For example, there is an available gap through the piece, the articulation wire and ancillary components can be inserted laterally instead of axially. This assembly option also allows the flexure to replaced without having to sever the articulation wire.

Figure 10:
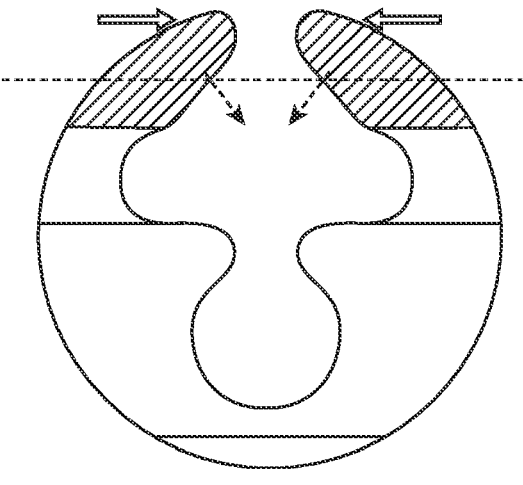
FIG. 10 is a cross section side view that depicts bending behavior of FIG. 9.

FIG. 10 is a cross section side view that depicts bending behavior of the embodiment depicted in FIGS. 8-9. During operation, the gap will tend to close as the flexure is articulated and will therefore minimize the possibility of having the ancillary components "escape" the inner profile lumens. If the presence of the gap is of concern, the component can still be manufactured with a gap and then "shape set" in order to close the gap before integration into an assembly.

Elements or components shown with any embodiment herein are exemplary for the specific embodiment and may be used on or in combination with other embodiments disclosed herein. While the invention is susceptible to various modifications and alternative forms, specific examples thereof have been shown in the drawings and are herein described in detail. The invention is not limited, however, to the particular forms or methods disclosed, but to the contrary, covers all modifications, equivalents and alternatives thereof.

What is claimed is:
1. A bending section to carry a tool for use in medical procedures, the bending section comprising:
a body including a first strut and a second strut; and
a channel formed through the body, the channel comprising:
a top portion defining a slot extending along a length of the channel and thereby separating the first strut from the second strut, the first and second struts extending parallel to a neutral axis of the body along the length of the channel;
a bottom portion extending along the length of the channel, wherein at least a section of the bottom portion of the channel has materials removed to form a plurality of gaps each shaped in a teardrop form tapering toward the bottom portion; and
a wire arranged along the bottom portion and configured to, when pulled, close a distance between the plurality of gaps and bend the body toward the bottom portion,
wherein the first strut and the second strut partially surround the channel.
2. The bending section of claim 1, wherein the cross section of the body is C-shaped.
3. The bending section of claim 2, wherein the first strut and the second strut are capable of bending toward a center of the cross section.

4. The bending section of claim 1, wherein the channel has a non-cylindrical cross-section.

5. The bending section of claim 1, wherein the bending section articulates an instrument comprising an end effector.

6. The bending section of claim 5, wherein the end effector is passable through the channel such that it is interchangeable.

7. The bending section of claim 5, wherein the end effector comprises forceps, scissors, a laser, a cautery tool, or a needle.

8. The bending section of claim 5, wherein the end effector comprises a pair of tines.

9. The bending section of claim 5, wherein the channel comprises a top pathway, a bottom pathway and a narrowed region therebetween connecting the top and bottom pathways.

10. The bending section of claim 5, wherein the channel further receives an ancillary component of the end effector.

11. The bending section of claim 10, wherein the ancillary component comprises fibers or electrical wires.

12. An apparatus to facilitate bending of an instrument comprising:

a wire;

a rod including a bendable section, the bendable section comprising:

a channel formed through a portion of the rod, wherein the rod has a non-uniform wall thickness such that the channel has a non-circular cross-section;

a strut portion extending along a length of the channel including a first and a second strut separated from each other by a slot of the channel; and a teardrop section extending along the length of the channel and positioned opposite the strut portion, wherein the teardrop section has materials removed to form a plurality of leaves that are separated from one another by a gap shaped in a teardrop form tapering away from the strut portion, wherein the bendable section is configured to bend when tension is applied to the wire.

13. The apparatus of claim 12, wherein the wire is configured to, when tension is applied to the tendon, close a distance between the plurality of gaps.

14. The apparatus of claim 12, wherein the rod is formed from a superplastic material.

15. The apparatus of claim 12, wherein the channel is configured to receive at least one ancillary component including one or more of a pull wire, an actuation wire, an optical fiber, an electrical wire, a pneumatic component, a hydraulic component, and an open lumen.

16. A medical apparatus, comprising:

a rod including a bending section that includes:

a channel formed through a portion of the rod, wherein the rod has a non-uniform wall thickness such that the channel has a non-circular cross-section;

a strut portion extending along a length of the channel including a first strut and a second strut separated from each other by a slot of the channel; and a teardrop section extending along the length of the channel and positioned opposite the strut portion, wherein the teardrop section has materials removed to form a plurality of leaves that are separated from one another by a gap shaped in a teardrop form tapering away from the strut portion.

17. The medical apparatus of claim 16, wherein the rod is formed from a superplastic material.

18. The medical apparatus of claim 16, wherein the channel is configured to receive at least one ancillary component including one or more of a pull wire, an actuation wire, an optical fiber, an electrical wire, a pneumatic component, a hydraulic component, and an open lumen.

19. The medical apparatus of claim 16, wherein the channel has a top portion and a bottom portion, and the top portion separates the first strut from the second strut, and wherein the bottom portion is wider than the top portion.

\* \* \* \* \*